United States Patent [19]

Nahas et al.

[11] Patent Number: 5,047,229
[45] Date of Patent: Sep. 10, 1991

[54] TREATMENT OF CARDIOVASCULAR AND CEREBRAL TOXICITY USING CALCIUM MODULATORS

[75] Inventors: Gabriel G. Nahas, Englewood, N.J.; Renaud Trouve, Maisons Alfort, France

[73] Assignee: Miles, Inc., Elkhart, Ind.

[21] Appl. No.: 943,639

[22] Filed: Dec. 17, 1986

[51] Int. Cl.$^5$ .............................................. A61K 49/00
[52] U.S. Cl. .................................... 424/10; 514/823; 514/922
[58] Field of Search .................. 424/10; 514/922, 823

[56] References Cited

PUBLICATIONS

Godfraind et al., "Calcium Entry Blockers in Cardiovascular and Cerebral Dysfunctions", pp. 1-322, Nijhoff Nahas et al., Chem. Abst., 105(1):528q (1986).
Fiedler et al., Chem. Abst., 103(17):134856n (1985).
Sato et al., Chem. Abst., 98(17):137409h (1983).
The Merck Index, 10th Ed., (1983), p. 318, No. 2217.
The Merck Index, 10th Ed., (1983), p. 489, No. 3366.
Nahas et al., (Nahas), The New England Journal of Medicine, "A Calcium-Channel Blocker as Antidote to the Cardiac Effects of Cocaine Intoxication", vol. 313, No. 8, Aug. 22, 1985, pp. 519-520.
Federation Proceedings, 45, Mar. 5, 1986, p. 1063, "Calcium Antagonists (5284-5289)", Nos. 5284-5289.
A. Fleckenstein, "Calcium Antagonism in the Heart and Smooth Muscle", John Wiley & Sons, New York, pp. 1-399, 1983.
T. Godfraind, A. G. Herman, D. Wellens, "Calcium Entry Blockers in Cardiovascular and Cerebral Dysfunctions", pp. 1-322, Martinus Nijhoff, Boston, 1984.

Primary Examiner—Stanley J. Friedman
Attorney, Agent, or Firm—Brumbaugh, Graves, Donohue & Raymond

[57] ABSTRACT

Calcium modulators can be effectively used to treat cardiovascular and cerebral toxicity induced by materials that alter the normal interaction of neurotransmitters with the calcium transport mechanisms of myocardial and cerebral cells. For example, calcium modulators can be used as an antidote to the lethal and chronic toxicity of cocaine and related indirectly acting sympathomimetic amines, imipramine and other tricyclic antidepressants, ganglionic stimulating drugs, and other toxic substances such as organophosphorus compounds that cause accumulations of neurotransmitters. Calcium modulators can also be used as an antidote to substances whose toxicity is based upon anticholinesterase activity. In addition, calcium modulators can be used as antagonists to the various types of toxic substances.

12 Claims, 1 Drawing Sheet

VERAPAMIL R=H
D600 R=OMe

NIFEDIPINE

DILTIAZEM

Ar=C$_6$H$_5$, CINNARIZINE
Ar=4-FC$_6$H$_4$, FLUNARIZINE

PERHEXILINE

PRENYLAMINE

TREATMENT OF CARDIOVASCULAR AND CEREBRAL TOXICITY USING CALCIUM MODULATORS

BACKGROUND OF THE INVENTION

The present invention relates to the use of calcium modulators in the treatment of cardiovascular and cerebral toxicity in mammals including man.

Calcium modulators are compounds that effect the transport of calcium through cellular membranes. Because of the several mechanisms for calcium transport, and the potential for multiple regulatory sites associated with some of these mechanisms, compounds of diverse structure have been found to be effective as calcium modulators. For example, reported calcium modulators include diphenylpiperazines such as verapamil and its derivatives, lidoflazine, cinnarizine and flunarizine; benzothiazepines such as diltiazem; dihydropyridines such as nifedipine, nitrendipine, nimodipine, nicardipine and BaK8644; and other structures such as bepridil, prenylamine and perhexiline. D. Wellans, "Twenty-Seven Calcium Entry Blockers in Cardiovascular and Cerebral Dysfunction" in *Calcium Entry Blockers in Cardio Vascular and Cerebral Dysfunction*, T. Godfraind et al. editors pp. 25-42 (1984).

As can be seen from the structures of the known calcium modulators shown in FIG. 1, the activity of a compound as a calcium modulator is not clearly associated with a particular type of structure. It has been established, however, that compounds that inhibit in vitro constriction of arteries induced by neurotransmitters such as norepinephrine, noradrenaline, and acetylcholine will generally act as calcium modulators in vivo. Fleckenstein, A. *Calcium Antagonism in the Heart and Smooth Muscle*, John Wiley and Sons, N.Y., (1983).

SUMMARY OF THE INVENTION

It has now been found that calcium modulators can be effectively used to treat cardiovascular and cerebral toxicity induced by substances that alter the normal interaction of neurotransmitters with the calcium transport mechanisms of capillaries of the heart and brain and in myocardial and cerebral cells. For example, calcium modulators can be used as an antidote to the lethal toxicity of cocaine and related indirectly acting sympathomimetic amines such as amphetamine and tyramine; as an antidote to tricyclic antidepressants such as imipramine, and ganglionic stimulating drugs such as nicotine; and as an antidote to other toxic substances such as organophosphorus compounds that cause accumulations of neurotransmitters and disrupted neurotransmitter activity. Calcium modulators can also be used as an antidote to substances whose toxicity is related to anticholinesterase activity. In addition, calcium modulators can be used as antagonists to the various types of toxic substances described above.

DETAILED DESCRIPTION OF THE INVENTION

Figure 1:
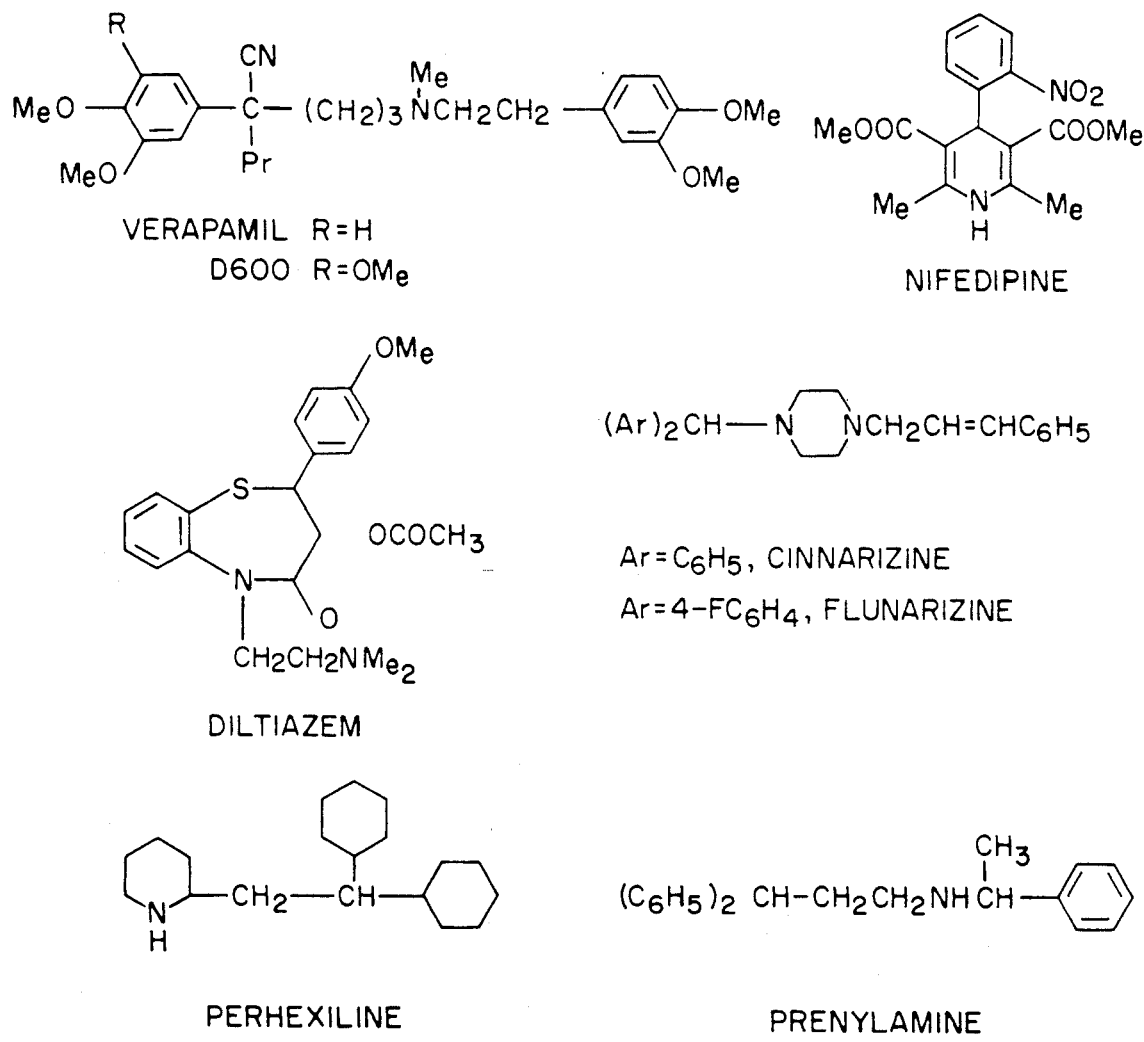
FIG. 1 shows the structures of a variety of known calcium modulators.

According to the invention, cardiovascular and cerebral toxicity induced by toxic materials that alter the normal interaction of neurotransmitters with the calcium transport mechanism of the capillaries of the heart and brain and in myocardial and cerebral cells can be treated by administering to a mammalian subject, including man, a compound which inhibits in vitro arterial constriction caused by the presence of norepinephrine or other neurotransmitters. In particular, the toxic effects of substances such as cocaine, imipramine, anticholinesterases, nicotine and organophosphorus compounds whose toxic effect is, at least in part, the result of an accumulation of neurotransmitters can be alleviated by administration of calcium modulators.

Suitable calcium modulators for use in the invention are generally those that will inhibit in vitro arterial constriction. Particularly suitable are those compounds, shown in FIG. 1, i.e. verapamil, D600, nifedipine, diltiazem, cinnarizine, flunarizine, perhexiline, prenylamine, and also nitrendipine, and nimodipine. The preferred compound for use in the treatment of cocaine intoxication according to the invention is nitrendipine.

Effective treatment in accordance with the invention requires prompt administration of the calcium modulator following exposure to the toxic material, preferably by intravenous administration. Alternatively, the calcium modulator can be used in accordance with the invention in anticipation of exposure to a toxic substance, such that it acts as an antagonist to the toxic effects. As an antagonist oral administration of calcium modulators is also possible.

Calcium modulators may also be combined with other known substances that function as antidotes to provide more effective treatment. In particular, where a toxic substance is known to have more than one mode of toxic effect, e.g. it effects both the neurotransmitter/calcium ion interaction and some other metabolic system, a second antidote compound directed to the second mode of toxic effect may be advantageously combined with the calcium modulator in the treatment according to the invention.

Furthermore, calcium modulators may help restore normal neurotransmitter activity in the brain of patients recovering from chronic intoxication with cocaine and other dependence producing drugs. Thus the claimed treatment method may be effective in easing the early phase of drug rehabilitation therapy and withdrawal from drug dependence.

The utilization of calcium modulators in accordance with the invention is further illustrated by way of the following examples. These results are provided for illustration only, however, and do not limit the scope of the invention.

EXAMPLE I

Ca$^{2+}$ Modulators as Antidotes to Imipramine

Imipramine is a tricyclic antidepressant that may induce life threatening complications, particularly when taken im excessive amounts. Two calcium modulators, flunarizine and nimodipine were tested for their ability to act as antidotes to lethal imipramine intoxication.

Fasting Sprague Dawley rats weighing 305±21 grams were fitted with a caudal artery catheter connected to a constant micro-infusion pump and to a recorder for the online recording of arterial blood pressure. A first group of ten rats received intraperitoneal injection of 100 mg/kg of imipramine. Five of the rats, the control group, were further treated with 10,μl/min of saline. The survival time of the five control rats was 14.6±5.5 minutes. Five test rats were given flunarizine at a rate of 0.1 mg/kg/min in saline. The test rats survived for 129±89 minutes (p<0.04).

In a second series of tests, thirteen rats received 85 mg/kg of imipramine by intraperitoneal injection. After the blood pressure of the rats had fallen to 50 mmHg, four control rats were treated with successive bolus of 0.3 ml of saline every 3 to 5 minutes until death occurred. Four other rats were treated every 5 to 10 minutes depending on blood pressure drop with successive bolus of saline and 373 μg/kg flunarizine. The total dose of flunarizine was 2.37±1.21 mg/kg in a saline volume of 4.9±0.72 ml. The remaining five rats were similarly treated with nimodipine, the total dosage of nimodipine being 0.36±0.11 mg/kg.

The four control rats survived for 17.0±6.0 minutes following injection of imipramine. All four of the rats treated with flunarizine, and four of the five rats treated with nimodipine survived, and were awake and active 24 hours later. Thus, both calcium modulators tested appeared to be effective in the treatment of acute imipramine poisoning.

EXAMPLE 2

$Ca^{2+}$ Modulators as Antidotes to Cocaine

Cocaine intoxication is associated with dysrythmia and myocardial infarction in healthy young adults, and can cause convulsions and death. The calcium modulator nitrendipine was tested for its effectiveness as an antidote to lethal doses of cocaine.

Ten fasting Sprague Dawley rats weighing 292±31 grams were fitted with a caudal artery catheter connected to a constant micro-infusion pump and to a recorder for the online recording of arterial blood pressure. A first group of five received intraperitoneal injection of 6mg/kg of cocaine, a lethal dose. Five other rats were given the same amount of cocaine followed by nitrendipine 4 to 5 minutes after the cocaine. Nitrendipine was given intra-arterially first in a loading dose of 7.4 g, followed by a constant infusion of 1.22 μg/kg/min lasting 85±22 minutes. (Total dose=129±23 μg/kg). The infusion was stopped when the rat was active and restless. The survival time of the five control rats was 8 min. 6 sec±5 min. 20 sec. Death could be attributed to convulsions and respiratory arrest. All five of the nitrendipine treated animals survived and 24 hours later were active and feeding themselves.

EXAMPLE 3

$Ca^{2+}$ Modulators as Antaqonists to Cocaine

Ten fasting Sprague Dawley rats weighing 292±31 grams were fitted with a caudal artery catheter connected to a constant micro-infusion pump and to a recorder for the online recording of arterial blood pressure. The recorder permitted monitoring of cardiac arrythmia.

In five control animals, cocaine was infused at a rate of 2 mg/kg/min. These animals exhibited frequent and sustained arrythmias. In addition, marked agitation, tremors and convulsions were observed, followed by death. The survival time of the control rats was 73±33 minutes with a dose of cocaine of 146±66 mg/kg.

When nitrendipine ($1.46 \times 10^{-3}$ mg/kg/min) was concurrently administered with the same dose of cocaine to five other rats, death occurred after 309±118 minutes (618 ±236 mg cocaine/kg). The heart rate throughout the infusion was stable, and no tremors or convulsions were observed. The cause of death in these five rats was apparently not cocaine intoxication, but rather was probably attributable to excess fluids due to the large infusion volume.

Tissue sections prepared from the hearts of the two sets of animals were also markedly different. The animals treated with cocaine alone exhibited disseminated areas of sarcolema disruption with liberation of disorganized myocardial fibers which present an appearance of waviness. Such alterations, which are symptomatic of the necrotic process leading to permanent infarcted lesions, were not observed in the animals treated with both cocaine and nitrendipine. Thus, nirendipine was effective not only to decrease the lethan toxicity of cocaine, but prevented the cardiac morphological lesions irreversibly produced by cocaine.

We claim:

1. A method for treating cardiovascular toxicity induced by a tricyclic antidepressant that induces a toxic effect by altering the normal interaction of neurotransmitters with the calcium ion metabolism of myocardial cells, comprising administering to a host intoxicated with the toxic material a compound which inhibits constriction of arteries in vitro in the presence of a neurotransmitter in an amount effective to treat the toxicity.

2. A method according to claim 1, wherein the compound administered is selected from the group consisting of verapamil, bepridil, nifedipine, diltiazem, cinnarizine, flunarizine, perhexiline, prenylamine, nitrendipine, nimodipine, nicardipine, and lidoflazine.

3. A method for treating cerebral toxicity induced by a tricyclic antidepressant that induces a toxic effect by altering the normal interaction of neurotransmitters with the calcium ion metabolism of cerebral cells, comprising administering to a host intoxicated with the toxic material a compound which inhibits constriction of arteries in vitro in the presence of a neurotransmitter in an amount effective to treat the toxicity.

4. A method according to claim 3, wherein the compound administered is selected from the group consisting of verapamil, bepridil, nifedipine, diltiazem, cinnarizine, flunarizine, perhexiline, prenylamine, nitrendipine, nimodipine, nicardipine, and lidoflazine.

5. A method according to claim 1, wherein the host is intoxicated with a lethal dose of the toxic material.

6. A method according to claim 3, wherein the host is intoxicated with a lethal dose of the toxic material.

7. A method according to claim 1, wherein the compound administered is nimodipine or flunarizine.

8. A method according to claim 1, wherein the compound administered is nimodipine or flunarizine.

9. A method for treating cardiovascular toxicity induced by imipramine comprising administering to a host intoxicated with imipramine a compound which inhibits constriction of arteries in vivo in the presence of a neurotransmitter in an amount effective to treat the toxicity.

10. A method according to claim 9, wherein the compound administered is selected from the group consisting of verapamil, bepridil, nifedipine, diltiazem, cinnarizine, flunarizine, perhexiline, prenylamine, nitrendipine, nimodipine, nicardipine, and lidoflazine.

11. A method for treating cerebral toxicity induced by imipramine comprising administering to a host intoxicated with imipramine a compound which inhibits constriction of arteries in vivo in the presence of a neurotransmitter in an amount effective to treat the toxicity.

12. A method according to claim 11, wherein the compound administered is selected from the group consisting of verapamil, bepridil, nifedipine, diltiazem, cinnarizine, flunarizine, perhexiline, prenylamine, nitrendipine, nimodipine, nicardipine, and lidoflazine.

* * * * *

UNITED STATES PATENT AND TRADEMARK OFFICE
CERTIFICATE OF CORRECTION

PATENT NO. : 5,047,229
DATED : September 10, 1991
INVENTOR(S) : Nahas et al.

It is certified that error appears in the above-identified patent and that said Letters Patent is hereby corrected as shown below:

Column 3, line 49, "Antaqonists" should read --Antagonists--;

Claim 1, line 6, "toxic material" should read --tricyclic antidepressant--;

Claim 3, line 6, "toxic material" should read --tricyclic antidepressant--;

Claim 5, line 2, "toxic material" should read --tricyclic antidepressant--;

Claim 6, line 2, "toxic material" should read --tricyclic antidepressant--;

Claim 8, line 1, "1" should read --3--.

Signed and Sealed this

Twenty-eighth Day of July, 1992

Attest:

DOUGLAS B. COMER

Attesting Officer      Acting Commissioner of Patents and Trademarks